US007160721B2

(12) United States Patent
Thomas et al.

(10) Patent No.: US 7,160,721 B2
(45) Date of Patent: Jan. 9, 2007

(54) COMPOSITION AND METHOD FOR INCREASING CELL DENSITY IN CELL CULTURES INFECTED WITH LENTIVIRUS

(75) Inventors: Anne Christine Thomas, Rochester, NH (US); Terry Kaleung Ng, Fort Dodge, IA (US)

(73) Assignee: Wyeth, Madison, NJ (US)

( * ) Notice: Subject to any disclaimer, the term of this patent is extended or adjusted under 35 U.S.C. 154(b) by 134 days.

(21) Appl. No.: 10/140,172

(22) Filed: May 7, 2002

(65) Prior Publication Data
US 2002/0197714 A1  Dec. 26, 2002

Related U.S. Application Data

(60) Provisional application No. 60/290,096, filed on May 10, 2001.

(51) Int. Cl.
*C12N 5/00* (2006.01)
*A61K 39/21* (2006.01)
(52) U.S. Cl. .................. 435/325; 424/184.1; 424/208.1
(58) Field of Classification Search ............ 424/184.1, 424/208.1; 435/325
See application file for complete search history.

(56) References Cited

U.S. PATENT DOCUMENTS

| 4,215,107 A | 7/1980 | Baynak et al. | |
| 4,533,637 A * | 8/1985 | Yamane et al. | ............. 435/371 |
| 5,534,408 A * | 7/1996 | Green et al. | .................... 435/5 |
| 5,846,825 A | 12/1998 | Yamamoto | |
| 5,958,423 A | 9/1999 | Chu | |
| 6,107,077 A | 8/2000 | Yamamoto | |

FOREIGN PATENT DOCUMENTS

| WO | WO 92/02530 A | 2/1992 |
| WO | WO 94/09792 | 5/1994 |

OTHER PUBLICATIONS

Clements et al., Molecular Biology and Pathogenesis of Animal Lentivirus Infections, Clinical Microbiology Reviews, Jan. 1996, vol. 9, No. 1, pp. 100-117.*
Navenot, J., et al., Molecular Anatomy of CCR5 Engagement by Physiologic and Viral Chemokines and HIV-1 Envelope Glycoproteins, J. Mol. Biol. 2001, vol. 313, pp. 1181-1193.
Yamamoto, J.K., et al., "Development of IL-2-Independent Feline Lymphoid Cell Lines Chronically Infected With Feline Immunodeficiency Virus: Importance for Diagnostic Reagents and Vaccines," *Intervirology*, vol. 32, No. 6, pp. 361-375, (1991).
Zapp, M. L., et al., "Small Molecules That Selectivity Block RNA Binding of HIV-1 Rev Protein Inhibit Rev Function and Viral Production," Cell, vol. 74, No. 6, pp. 969-978, Sep. 24, 1993.
Navenot, J. et al., "Molecular Anatomy of CCR5 Engagement by Physiologic and Viral Chemokines and HIV-1 Envelope Glycoproteins: Differences in Primary Structural Requirements for RANTES, MIP-1a, and vMIP-II Binding," *J. Mol. Biol.*, (2001), 313(5):1181-93.

* cited by examiner

*Primary Examiner*—Stacy B. Chen
(74) *Attorney, Agent, or Firm*—Finnegan, Henderson, Farabow, Garrett & Dunner, LLP

(57) ABSTRACT

A composition and method for enhancing cell growth and increasing the density of cell cultures containing lentivirus-infected host cells comprises adding a suitable quantity of an antibiotic to the culture to destroy harmful bacteria.

51 Claims, No Drawings

COMPOSITION AND METHOD FOR INCREASING CELL DENSITY IN CELL CULTURES INFECTED WITH LENTIVIRUS

FIELD OF THE INVENTION

The present invention relates to novel cell cultures. In particular, the invention is directed to new cell cultures infected with lentiviruses, such as feline immunodeficiency virus (FIV), which contain a suitable antibiotic to increase the cell density and enhance the growth of the culture. The invention also relates to new methods for increasing the density of cell cultures using certain antibiotics.

BACKGROUND OF THE INVENTION

Lentiviruses constitute a class of viruses which can lead to a variety of diseases in both humans and animals. These diseases are often preceded by several months or even years of incubation. For example, the pathologies associated with AIDS are caused by the human immunodeficiency viruses (HIVs) and result from a chronic progression of the disease, often times causing cachexia and death in the patient several years after infection.

Lentiviruses have also been associated with various pathologies in such species as apes and monkeys, as well as domesticated animals such as horses, burros, cattle, goats, and sheep. Among these, equine infectious anemia (EIA) has been characterized as the most important infectious disease of horses occurring throughout the world. Lentiviruses of sheep are relatively common pathogens in most parts of the world, and include Maedi-visna virus and progressive pneumonia virus as two predominate types. Bovine immunodeficiency virus is an important cause of illness in cattle.

Other lentiviruses are vital indicators of pathology in animals such as cats. Feline immunodeficiency virus, structurally similar to HIV, can cause death in house cats. Increasingly, doctors, veterinarians, and researchers are devoting considerable time and resources to preventing and treating diseases caused by these viruses.

Part of the research involves growing tissue cultures containing cells, for example lymphocytes, which have been infected with one or more of the known lentiviruses. Lymphocyte cultures or anchorage dependent epithelium-like cells such as feline kidney cell cultures may be grown in T-flasks, roller bottles, spinner flasks and bioreactors using media such as Minimal Essential Media (MEM), Roswell Park Memorial Institute (RPMI), Dulbecco's MEM (DMEM), and AIM V (Gibco/LTI, Grand Island, N.Y.) supplemented with bovine serum up to about 20% and up to about 5% bovine serum albumin (BSA). Large-scale cultures may be grown in large spinners, fermentor, and bioreactors in the presence of shear protective chemical, thickener, emulsifiers or compounds such as methylcellulose, carboxylmethyl cellulose, and surfactants such as the Pluronic series, e.g. PLURONIC® F-68, manufactured by BASF Corporation of Wyandotte, Mich.

In maintaining tissue cultures containing viruses, researchers seek to destroy harmful bacteria within the culture so that the cells containing the virus can grow and propagate. At the same time, a concomitant goal is to maximize growth of the cell culture. To facilitate growth and destroy bacteria, it has been accepted practice to add antibiotics, usually a combination thereof, to the cell culture. For example, U.S. Pat. No. 5,958,423 sets forth a cell culture of Madin-Darby Bovine Kidney (MDBK) cells in which up to 30 mcg/mL of polymixin B and neomycin, and up to 2.5 mcg/mL of amphotericin B is utilized.

What is now needed in the art are new cell culture compositions containing cells infected with lentiviruses. Especially needed are novel cell cultures in which cell growth can be maximized and the presence of harmful organisms such as bacteria can be simultaneously minimized. Also needed are new methods of growing cell cultures in which the density thereof can be increased through the promotion of tissue growth. Further needed are new additives which can optimize the density of cell cultures by enabling and enhancing the growth of the cells which comprise the culture.

SUMMARY OF THE INVENTION

In one embodiment, the present invention is directed to a cell culture comprising at least one lentivirus-infected host cell and a growth-promoting amount of an antibiotic consisting essentially of neomycin or a biologically compatible salt thereof.

The invention is also directed to a cell culture which contains at least one lentivirus-infected host cell and neomycin or a biologically compatible salt thereof, such that neomycin is present substantially without another antibiotic in an amount which is effective at inhibiting bacterial growth and increasing the density of the cell culture.

Also provided as part of the invention is a method for increasing the density of a cell culture in which cells therein have been infected with a lentivirus, which involves adding an antibiotic consisting essentially of neomycin or a biologically acceptable salt thereof to the cell culture.

The invention also provides a composition suitable for addition to a cell culture infected with lentivirus. The composition contains a cell density enhancing quantity of an antibiotic consisting essentially of neomycin or a biologically salt thereof, along with at least one cell culture supplement. The cell culture supplement is desirably bovine-derived sera.

The foregoing and other features and advantages of the invention will become more apparent from the detailed description of the preferred embodiments of the invention given below.

DETAILED DESCRIPTION OF THE PREFERRED EMBODIMENTS

The present invention is directed to cell cultures. Those contemplated for use herein are those suitable for research and study which are capable of harboring lentiviruses and permitting the growth thereof. Such cell cultures would therefore include lymphocytes and other types of cells which can become infected with one or more lentiviruses. Other suitable cell cultures would include feline lymphocytes, fibroblast-like and epithelium-like cells such as feline kidney cells, Crandell Feline Kidney or CRFK cells, FL6, FL72 and FL 74 (Feline Lymphocyte) cells. T-cell lymphocytes may be preferred for use herein, as well as IL-2 independent FetJ and FL6 lymphocytes.

The term "lentiviruses' is used herein to encompass all known and yet-to-be-discovered lentiviruses, including without limitation equine infectious anemia virus, Maedi-visna virus, progressive pneumonia virus, caprine arthritis-encephalitis virus, feline immunodeficiency virus (FIV), simian immunodeficiency viruses infecting such species as the macaque, and African monkeys and baboons, and the human immunodeficiency virus (HIV) Types I and II. The term "lentiviruses" also includes analogs, derivatives and peptide sequences of any of the foregoing. Preferred for use herein are the non-human lentiviruses, and in particular, feline immunodeficiency virus (FIV).

The cell cultures of the invention may be cultivated using methods known in the art. For example, the host cells such as lymphocytes may be chronically infected with one or more of the foregoing lentiviruses using accepted procedures, and then grown in suitable media. Preferably, the media is substantially liquid media. Even more preferably, the media is initially provided as substantially serum-free media. The host cells may be suspended in the liquid media, for example. Cell density of the cultivated cell culture may vary according to the particular host cells, the media, and the growth chamber, but can be within the range of about $1 \times 10^4$ to about $1 \times 10^6$ suitable cells per milliliter (mL) of cell culture (including media). More preferably, the cell density is about $2 \times 10^5$ to about $5 \times 10^5$ cells per milliliter.

As a further part of the invention, the cell cultures contain a suitable antibiotic which is effective at inhibiting the growth of bacteria within the culture, while at the same time increasing the growth of the cells and thereby increasing the density of the cell culture. Preferred for use herein is the antibiotic neomycin, which would include all biologically compatible salts and derivatives thereof, such as neomycin sulfate. By "biologically compatible" it is meant that the salt or derivative thereof has substantially no adverse biological effects upon the cell.

The quantity of neomycin included in the cell culture may vary according to the needs of the skilled artisan, but is typically included in an amount that will increase the density of the cell culture. An amount of neomycin within the range of from about 5 micrograms/mL of cell culture to about 60 micrograms/mL of cell culture (including media) is usually preferred. In a more preferred embodiment, neomycin is included in the cell culture in a quantity of at least about 10 micrograms/mL, and more preferably at least about 20 micrograms/mL. Even more desirably, the quantity of neomycin will be within about 30 micrograms/mL to about 60 micrograms/mL.

It is preferred to utilize neomycin to enhance cell culture growth and density without the inclusion of such other antibiotics as polymixin B and gentamycin, for example. Polymixin B may be derived from polymixin $B_1$ and $B_2$, which are produced by the growth of Bacillus polymyxa (Prazmowski) Migula (Fam. Bacillaceae). It has now been found that including both neomycin and polymixin B in cell culture can, in many instances, result in a significantly smaller increase in cell density when compared with the use of neomycin alone.

Other components of the cell culture of the invention would typically include at least one culture supplement. The culture supplement may be bovine-derived, such as from bovine sera, and can include bovine serum and bovine serum albumin (BSA). The culture supplement may be included in amounts of from about 0.1 to about 10% by volume of the final cell culture.

The use of neomycin as herein described may increase cell density by at least about 20%, and more preferably by at least about 33 ⅓% over an identical cell culture of lentivirus-infected host cells not containing any antibiotic. Cell density may be assessed by acceptable methods, including the use of trypan blue exclusion on hemacytometer.

The following example is provided to illustrate one preferred aspect of the invention, but should not be construed as limiting the scope thereof.

EXAMPLE

In this example, Fet-J cells chronically infected with feline immunodeficiency virus (FIV) were grown in serum free media such as modified DMEM:F12 Media or AIM V media, supplemented with 2.5 mg/mL of ALBUMAX®, which is derived from BSA. Cells were grown in suspension in Erlenmeyer flasks on a rotary shaker at 150 rpm at 37° C. Cells were planted at a cell density of $3 \times 10^5$ viable cells/mL. Cell densities were determined by trypan blue exclusion on hemacytometer. Gp 120 expression determination was accomplished by enzyme linked immunosorbent assay (ELISA) using anti-FIV Gp 120 monoclonal antibodies. The antibiotics assessed for FIV supplementation included gentamycin, neomycin and polymixin B. Media were spiked with respective antibiotics at a concentration of 30 micrograms/mL. Cell densities were determined on a 24 hour basis by the method described above. The results are shown in TABLE 1.

TABLE 1

| Experimental Group | Antibiotic Concentration (micrograms/mL) | Day 0 (cell/mL) | Day 1 | Day 2 | Day 3 | Day 4 | Day 5 |
|---|---|---|---|---|---|---|---|
| Control | N/A | $3.0 \times 10^5$ | $3.6 \times 10^5$ | $5.5 \times 10^5$ | $1.0 \times 10^6$ | $1.2 \times 10^6$ | $1.2 \times 10^6$ |
| Gentamycin | 30 μg/mL | $3.0 \times 10^5$ | $2.4 \times 10^5$ | $3.2 \times 10^5$ | $6.5 \times 10^5$ | $1.1 \times 10^6$ | $1.1 \times 10^6$ |
| Neomycin | 30 μg/mL | $3.0 \times 10^5$ | $4.7 \times 10^5$ | $7.8 \times 10^5$ | $1.2 \times 10^6$ | $1.3 \times 10^6$ | $1.8 \times 10^6$ |
| Polymixin B | 30 μg/mL | $3.0 \times 10^5$ | $2.9 \times 10^5$ | $4.6 \times 10^5$ | $5.8 \times 10^5$ | $6.6 \times 10^6$ | $6.6 \times 10^5$ |
| Polymixin B + Neomycin | 30 μg/mL + 30 μg/mL | $3.0 \times 10^5$ | $2.9 \times 10^5$ | $5.0 \times 10^5$ | $7.0 \times 10^5$ | $7.7 \times 10^5$ | $7.8 \times 10^5$ |

The results from Table 1 show that the cell culture suspensions supplemented with neomycin had the best overall growth and increase in cell densities. Gentamycin had no significant effect, with daily cell densities being substantially the same as the controls. Cultures supplemented with Polymixin B, or neomycin together with polymixin B actually suppressed cell density as compared to the cultures in which no antibiotic was utilized and thus were also much less dense than those wherein neomycin by itself was used.

Although the invention has been described with reference to particular embodiments thereof, it should be appreciated that many changes and modifications can be made without departing from the spirit or scope of the invention. Accordingly, the invention is not to be considered as limited by the foregoing description, but is only limited by the scope of the appended claims.

The invention claimed is:

1. A cell culture comprising at least one lentivirus-infected host cell and a growth promoting amount of an antibiotic consisting essentially of neomycin or a biologically compatible salt or derivative thereof, wherein said lentivirus is selected from the group consisting of equine infectious anemia virus, Maedi-visna virus, progressive pneumonia virus, caprine arthritis-encephalitis virus, feline immunodeficiency virus (FIV), and simian immunodeficiency virus, and wherein the antibiotic increases the density of the cell culture by at least about 20% over a cell culture of lentivirus-infected host cells not containing any of said antibiotic.

2. The cell culture of claim 1, wherein said neomycin is present in an amount of up to about 60 micrograms/mL of said culture.

3. The cell culture of claim 1, wherein said virus is selected from the group consisting of feline immunodeficiency virus (FIV) and simian immunodeficiency virus.

4. The cell culture of claim 3, wherein said virus is feline immunodeficiency virus (FIV).

5. The cell culture of claim 1, wherein said host cell is a lymphocyte.

6. The cell culture of claim 5, wherein said lymphocyte is a T-cell.

7. The cell culture of claim 6, wherein said lymphocyte is selected from the group consisting of IL-2 independent FetJ and FL6 lymphocytes.

8. The cell culture of claim 1, wherein said neomycin is present in an amount of from about 5 micrograms/mL.

9. The cell culture of claim 8, wherein said quantity of neomycin is effective at increasing the density of said cell culture.

10. The cell culture of claim 9, wherein said quantity of neomycin is effective at inhibiting bacterial growth in said cell culture.

11. The cell culture of claim 10, wherein said neomycin is present in an amount of from about 20 micrograms/mL.

12. The cell culture of claim 11, wherein said neomycin is present in an amount of from about 30 micrograms/mL.

13. The cell culture of claim 4, wherein said cell culture is present in serum-free media.

14. The cell culture of claim 11, wherein the cells of said cell culture are planted at a density within the range of about $1 \times 10^5$ to about $5 \times 10^5$ viable cells/mL of cell culture.

15. The cell culture of claim 14, wherein the cells of said cell culture are planted at a density of about $3 \times 10^5$ viable cells/mL.

16. A cell culture comprising at least one lentivirus-infected host cell and neomycin, wherein said neomycin is present substantially without another antibiotic in an amount which is effective at inhibiting bacterial growth and increasing the density of said cell culture by at least about 20% over a cell culture of lentivirus-infected host cells not containing any of said antibiotic, wherein said lentivirus is selected from the group consisting of equine infectious anemia virus, Maedi-visna virus, progressive pneumonia virus, caprine arthritis-encephalitis virus, feline immunodeficiency virus (FIV), and simian immunodeficiency virus.

17. The cell culture of claim 16, wherein said cell culture contains substantially no gentamycin or polymixin B.

18. The cell culture of claim 16, wherein said neomycin is present in said cell culture in an amount within the range of from about 5 micrograms/mL to about 60 micrograms/mL of said cell culture.

19. The cell culture of claim 18, wherein said neomycin is present in said cell culture in an amount of at least about 20 micrograms/mL.

20. The cell culture of claim 19, wherein said neomycin is present in said cell culture in an amount of at least about 30 micrograms/mL.

21. The cell culture of claim 16, wherein said virus is selected from the group consisting of feline immunodeficiency virus (FIV) and simian immunodeficiency virus.

22. The cell culture of claim 21, wherein said virus is feline immunodeficiency virus (FIV).

23. The cell culture of claim 16, wherein said host cell is a lymphocyte.

24. The cell culture of claim 23, wherein said lymphocyte is a T-cell.

25. The cell culture of claim 24, wherein said lymphocyte is selected from the group consisting of IL-2 independent FetJ and FL6 T-lymphocytes.

26. The cell culture of claim 16, wherein the cells of said cell culture are planted at a density within the range of about $1 \times 10^5$ to about $5 \times 10^5$ viable cells/mL.

27. The cell culture of claim 26, wherein the cells of said cell culture are planted at a density of about $3 \times 10^5$ viable cells/mL.

28. A method for increasing the density of a cell culture in which cells therein have been infected with a lentivirus, which comprises adding an antibiotic consisting essentially of neomycin to said cell culture, wherein said lentivirus is selected from the group consisting of equine infectious anemia virus, Maedi-visna virus, progressive pneumonia virus, caprine arthritis-encephalitis virus, feline immunodeficiency virus (FIV) and simian immunodeficiency virus.

29. The method of claim 28, wherein said neomycin is added in an amount of from about 5 micrograms/mL to about 60 micrograms/mL of cell culture.

30. The method of claim 29, wherein said neomycin is added in an amount which is effective at inhibiting bacterial growth in said cell culture.

31. The method of claim 30, wherein said neomycin is added in an amount of at least about 20 micrograms/mL.

32. The method of claim 31, wherein said neomycin is added in an amount of at least about 30 micrograms/mL.

33. The method of claim 28, which further comprises planting said cell culture to a density within the range of from about $1 \times 10^5$ to about $5 \times 10^5$ viable cells/mL.

34. The method of claim 33, in which said cell culture is planted at a density of about $3 \times 10^5$ viable cells/mL.

35. The method of claim 28, further comprising adding at least one culture supplement to said cell culture.

36. The method of claim 35, wherein said culture supplement is bovine serum albumin (BSA).

37. The method of claim 28, wherein said neomycin is effective at increasing cell density by at least about 20%.

38. The method of claim 37, wherein said neomycin is effective at increasing cell density by at least about 33 ⅓%.

39. The method of claim 38, wherein said neomycin is effective at increasing cell density by at least about 50%.

40. A method for cultivating a cell culture of lentivirus-infected cells, which comprises adding neomycin substantially without polymixin B or gentamycin to said culture, wherein said lentivirus is selected from the group consisting of equine infectious anemia virus, Maedi-visna virus, progressive pneumonia virus, caprine arthritis-encephalitis virus, feline immunodeficiency virus (FLV) and simian immunodeficiency virus.

41. The method of claim 40, wherein said neomycin is added in a quantity within the range of about 5 micrograms/mL to about 60 micrograms/mL of cell culture.

42. The method of claim 41, wherein said quantity of neomycin is effective at inhibiting bacterial growth in said cell culture.

43. The method of claim 41, wherein said quantity of neomycin is at least about 20 micrograms/mL of cell culture.

44. The method of claim 43, wherein said quantity of neomycin is at least about 30 micrograms/mL of cell culture.

45. The method of claim 40, further comprising adding an effective quantity of at least one cell culture supplement to said culture.

46. The method of claim 45, wherein said cell culture supplement is bovine serum albumin (BSA).

47. The method of claim 40, further wherein said cell culture contains lymphocyte cells.

48. The method of claim 47, wherein said virus is selected from the group consisting of feline immunodeficiency virus (FIV) and simian immunodeficiency virus.

49. A cell culture composition, comprising:
a) from about $1 \times 10^5$ to about $5 \times 10^5$ viable cells/mL of Fet-J cells chronically infected with feline immunodeficiency virus;
b) at least about 10 micrograms/mL of an antibiotic consisting essentially of neomycin or a biologically compatible salt or derivative thereof, wherein the antibiotic increases the density of the cell culture by at least about 20% over a cell culture of feline immunodeficiency virus-infected Fet-J cells not containing any of said antibiotic.

50. The cell culture of claim 1, wherein the density of said cell culture is increased by at least about 33 ⅓%.

51. The cell culture of claim 16, wherein the density of said cell culture is increased by at least about 33 ⅓%.

* * * * *

UNITED STATES PATENT AND TRADEMARK OFFICE
CERTIFICATE OF CORRECTION

PATENT NO. : 7,160,721 B2
APPLICATION NO. : 10/140172
DATED : January 9, 2007
INVENTOR(S) : Anne Christine Thomas and Terry Kaleung Ng It is certified that error appears in the above-identified patent and that said Letters Patent is hereby corrected as shown below:

Column 7, line 2, "(FLV)" should read --(FIV)--.

Signed and Sealed this

Seventeenth Day of April, 2007

JON W. DUDAS
*Director of the United States Patent and Trademark Office*